(12) United States Patent
Arora et al.

(10) Patent No.: US 8,021,323 B2
(45) Date of Patent: Sep. 20, 2011

(54) SOFT TISSUE AUGMENTATION BY NEEDLE-FREE INJECTION

(75) Inventors: Anubhav Arora, Goleta, CA (US); Samir Mitragotri, Goleta, CA (US); Ahmet Tezel, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/179,843

(22) Filed: Jul. 25, 2008

(65) Prior Publication Data
US 2009/0030367 A1 Jan. 29, 2009

Related U.S. Application Data

(60) Provisional application No. 60/952,310, filed on Jul. 27, 2007.

(51) Int. Cl.
*A61M 5/30* (2006.01)
(52) U.S. Cl. .................................................. 604/68
(58) Field of Classification Search .............. 604/68, 604/69, 70, 117, 118, 93.01
See application file for complete search history.

(56) References Cited

U.S. PATENT DOCUMENTS

| 6,689,095 B1 | 2/2004 | Garitano et al. |
| 2006/0089594 A1* | 4/2006 | Landau .................. 604/68 |

OTHER PUBLICATIONS

AMI "Jet Injector Medical Presentation," www.ameditech.com/medinfo/jet.html, pp. 1-9.

* cited by examiner

*Primary Examiner* — Nicholas D Lucchesi
*Assistant Examiner* — Brooke M Matney
(74) *Attorney, Agent, or Firm* — Linda A. Fox; Stephen Donovan; Debra Condino

(57) ABSTRACT

The invention relates to needle-free apparatus that can be used to augment soft tissue. More specifically, the needle-free injectors of the present invention allow injection of more viscous materials such as collagen, hyaluronic acid, and other polymers that are useful as dermal fillers. The needle-free injectors of the present invention allow injection of such materials to fill the undesired lines, wrinkles, and folds of a patient. The present invention also relates to kits comprising such needle-free injectors and a quantity of dermal filling material. In addition, the present invention relates to methods of augmenting soft tissue using needle-free apparatus.

28 Claims, 9 Drawing Sheets

SOFT TISSUE AUGMENTATION BY NEEDLE-FREE INJECTION

RELATED APPLICATION

This application claims priority to U.S. Provisional Patent Application No. 60/952,310 filed on Jul. 27, 2007, which is incorporated herein by reference.

BACKGROUND OF THE INVENTION a. Field of the Invention

The invention relates to methods for augmenting soft tissue using a needle-free jet injector, and to the needle-free injectors useful for such methods. The present invention is particularly useful for augmenting skin using a needle-free jet injector to fill lines, folds, and wrinkles in skin with dermal fillers such as collagen, hyaluronic acid, or a variety of biodegradable and nonbiodegradable polymers.

b. Background Art

Figure 1A:
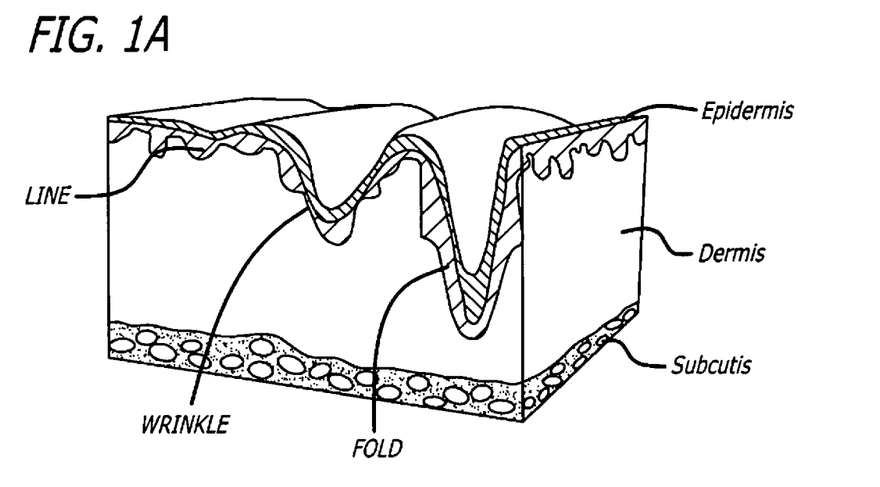
FIG. 1A depicts a cross section of animal or human skin, showing the epidermal, dermal, and subcutaneous layers, and showing lines, wrinkles, and folds on such skin.

As skin ages and is repeatedly exposed to the sun's ultra violet rays, dermal cells decrease their production of hyaluronic acid and increase the rate of its degradation. Likewise, aging skin loses collagen, another natural substance necessary to keep skin youthful and resilient. As shown in FIG. 1A, over time, the loss of hyaluronic acid and collagen causes aging skin to develop lines, wrinkles, and folds.

For the past few decades, patients have had a variety of options for augmenting soft tissue to fill undesired lines, wrinkles, folds, and scars. Originally, collagen was used for such soft tissue augmentation. More recently, hyaluronic acid in a variety of formulations has gained in popularity. Additionally, a variety of biodegradable and nondegradable products have been introduced or are in the process of regulatory approval for use as dermal fillers.

Figure 1B:
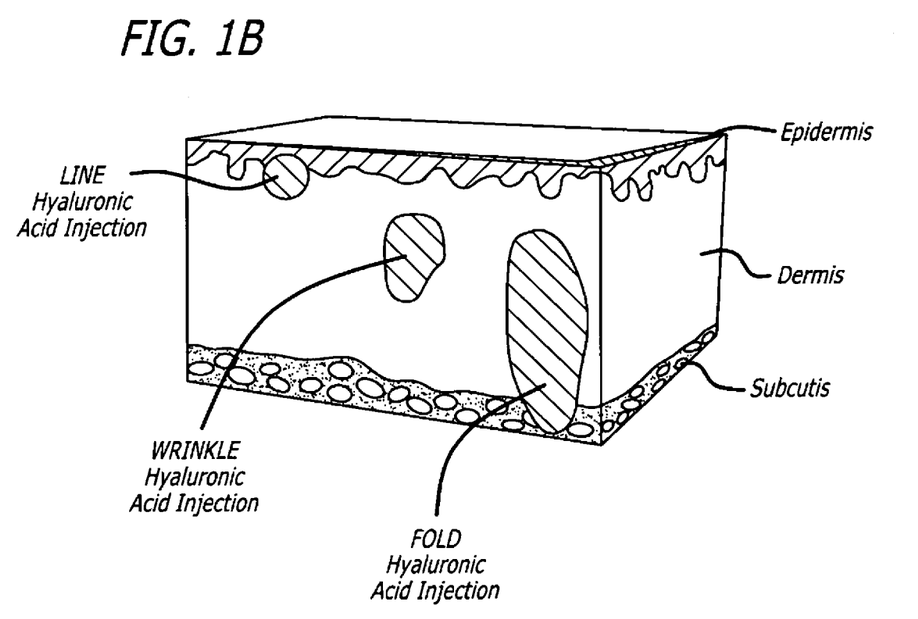
FIG. 1B depicts the cross section of animal or human skin shown in FIG. 1A, showing injection sites for hyaluronic acid for filling lines, wrinkles, and folds.

As shown in FIG. 1B, these soft tissue augmentation products are typically injected with a needle just below the surface of the skin, at the site of the wrinkle, line, or fold (or scar or dermal tissue to be enhanced). The products essentially plump up the skin from beneath the upper layers of skin. Some soft tissue augmentation products are instead implanted beneath the skin with an incision. In either case, the skin is cut or punctured with a needle or scalpel type instrument to insert soft tissue augmentation products into the desired location.

Use of needles and similar instruments puts health workers and patients at risk of infection through inadvertent needle-sticks or other equipment misuse. Additionally, needles and syringes are difficult to sterilize, and the use of improperly sterilized syringes and needles greatly increases the risk of blood-borne disease transmission among patients. While disposable syringes are typically used to alleviate the risk of disease transmission, these disposable units create hazardous medical waste and waste disposal problems. It is thus desirable to have a system for administering soft tissue augmentation products without the use of needles or similar devices.

In the 1930s, the first needle-free injectors were invented and patented. In the late 1940's, Hingson and Hughes reported a series of clinical, anatomical, and histological studies on jet injection of several drugs, in particular insulin, using a device called Hypospray. Interest in needle-free injection was substantially increased and jet injectors were used with several other drugs including penicillin, streptomycin, sulfones and vaccines against typhoid, diphtheria and tetanus, polio, and small pox.

Single-dose jet injectors, known as DCJIs (Disposable Cartridge Jet Injectors), are currently available and have been used for delivering insulin, growth hormones, vaccines as well as a variety of liquid drugs. Some DCJIs are only partly disposable (a disposable liquid reservoir in conjunction with a non-disposable actuation mechanism) while others are fully disposable.

Multidose jet-injectors were first described in the 1950s. Introduction of multi-use-nozzle jet injectors opened the door to mass immunization. The Press-O-Jet and Ped-O-Jet injectors were used for mass immunization against numerous diseases including poliomyelitis, influenza, typhoid, cholera, yellow fever, and smallpox all around the world.

Such jet injectors are typically used for intramuscular injection of typically freely-flowing liquid drugs. It is desirable to adapt a liquid jet injector for fairly accurate subdermal injection of viscous materials for soft tissue augmentation.

BRIEF SUMMARY OF THE INVENTION

The present invention relates to apparatus that is needle-free and is useful for augmenting the soft tissue of a patient, in particular, for filling the undesired lines, wrinkles and folds of a patient. In one aspect of the present invention, an apparatus for needle-free injection of a soft tissue augmentation material comprises a main body comprising a chamber for containing the soft tissue augmentation material, a drive mechanism for exerting forces on the soft tissue augmentation material in said chamber to expel the soft tissue augmentation material, and a nozzle having a first end and a second end, the first end being connected to the main body and the second end located distal to the main body. In one embodiment, the needle-free injector comprises a cartridge prefilled with at least one soft tissue augmentation material, wherein the cartridge can be inserted into the chamber. In another embodiment, the cartridge is prefilled with hyaluronic acid.

In yet another embodiment, the needle-free apparatus comprises at least one spacer that is capable of connecting to the second end of the nozzle. The at least one spacer separates the end of the nozzle from the injection site, thereby allowing more precise placement of a dermal filler material within the dermal layers of a patient. For example, for filling a line, it is desirable to be able to inject the dermal filler into a shallower layer of the dermis. A spacer increases the distance between the nozzle of the needle-free apparatus and the skin, thereby allowing for shallower deposition of the dermal filler. In one embodiment, the spacer is at least about 1 mm wide. In another embodiment, the spacer is about 5 mm wide. In yet another embodiment, the needle-free apparatus comprises a plurality of spacers that are interchangeable and connectable to one another.

In another embodiment of the present invention, the needle-free apparatus is disposable and comes prefilled with a dermal filler such as hyaluronic acid or collagen.

The present invention also relates to a needle-free injector for injecting dermal fillers into the skin of a human patient. Such needle-free injectors comprise a main body, a dosage drum connected to the main body, and a nozzle with a first end and a second end, wherein the first end is capable of connecting to the main body and the second end is distal to the first end. In one embodiment, the nozzle diameter is less than about 500 µm. In another embodiment, the nozzle diameter is less than about 200 µm.

In another embodiment, the needle-free injector also comprises at least one spacer that is capable of connecting to the second end of the nozzle. In one embodiment, the spacer is between about 2 mm wide to about 10 mm wide. In another embodiment, the spacer is about 5 mm wide. In yet another embodiment, the needle-free injector has a plurality of spacers that are interchangeable, come in a variety of widths, and are capable of connecting to one another. In yet another embodiment, the plurality of spacers range in size from about 1 mm to about 10 mm.

In a further embodiment of the present invention, the dosage drum of the needle-free injector is prefilled with a quantity of a dermal filler material. In yet another embodiment, the needle-free injector is prefilled with hyaluronic acid.

The present invention also relates to kits for soft tissue augmentation. The kits comprise a needle-free apparatus and a quantity of at least one soft tissue augmentation material. In one embodiment, the needle-free apparatus has a main body with a chamber for containing the soft tissue augmentation material, a drive mechanism for exerting forces on the soft tissue augmentation material to expel it, and a nozzle having a first end and a second end, the first end being connected to the main body and the second end located distal to the main body. In another embodiment, the needle-free apparatus has at least one spacer that is capable of connecting to the second end of the nozzle. In another embodiment, the soft tissue augmentation material supplied in the kit is hyaluronic acid. In yet another embodiment, the hyaluronic acid in the kit is supplied in at least one cartridge that may be disposable and that can be inserted into the chamber of the needle-free apparatus. In another embodiment, the needle-free apparatus of the kit is disposable. In a further embodiment, the disposable needle-free apparatus is prefilled with a quantity of the soft tissue augmentation material.

The present invention further relates to methods of filling undesired folds, wrinkles, or lines in a patient, comprising filling a needle-free injector with a quantity of a dermal filler material and using the needle-free injector to administer the dermal filler to the undesired folds, wrinkles, or lines. In one embodiment, the method further includes connecting at least one spacer to the second end of the nozzle of the needle-free injector before filling an undesired fold, wrinkle, or line of a patient.

This invention also relates to methods for augmenting the soft tissue of a patient by filling a needle-free apparatus contained in a kit with at least one soft tissue augmentation material and injecting the soft tissue augmentation material with the needle-free injector. In a further embodiment, the method includes connecting at least one spacer to the second end of the nozzle of the needle-free apparatus, filling the chamber of the needle-free apparatus with hyaluronic acid that is also provided in the kit, placing the spacer end of the needle-free injector against a portion of the patient's skin to be augmented, and using the needle-free injector to inject a volume of hyaluronic acid into the patient's skin.

The foregoing and other aspects, features, details, utilities, and advantages of the present invention will be apparent from reading the following description and claims, and from reviewing the accompanying drawings.

DETAILED DESCRIPTION OF THE INVENTION

The present invention generally relates to methods for needle-free injection of materials for soft tissue augmentation, needleless or needle-free injectors useful for injecting soft tissue augmentation materials, and to kits comprising such needleless injectors and materials useful for soft tissue augmentation.

Figure 2:
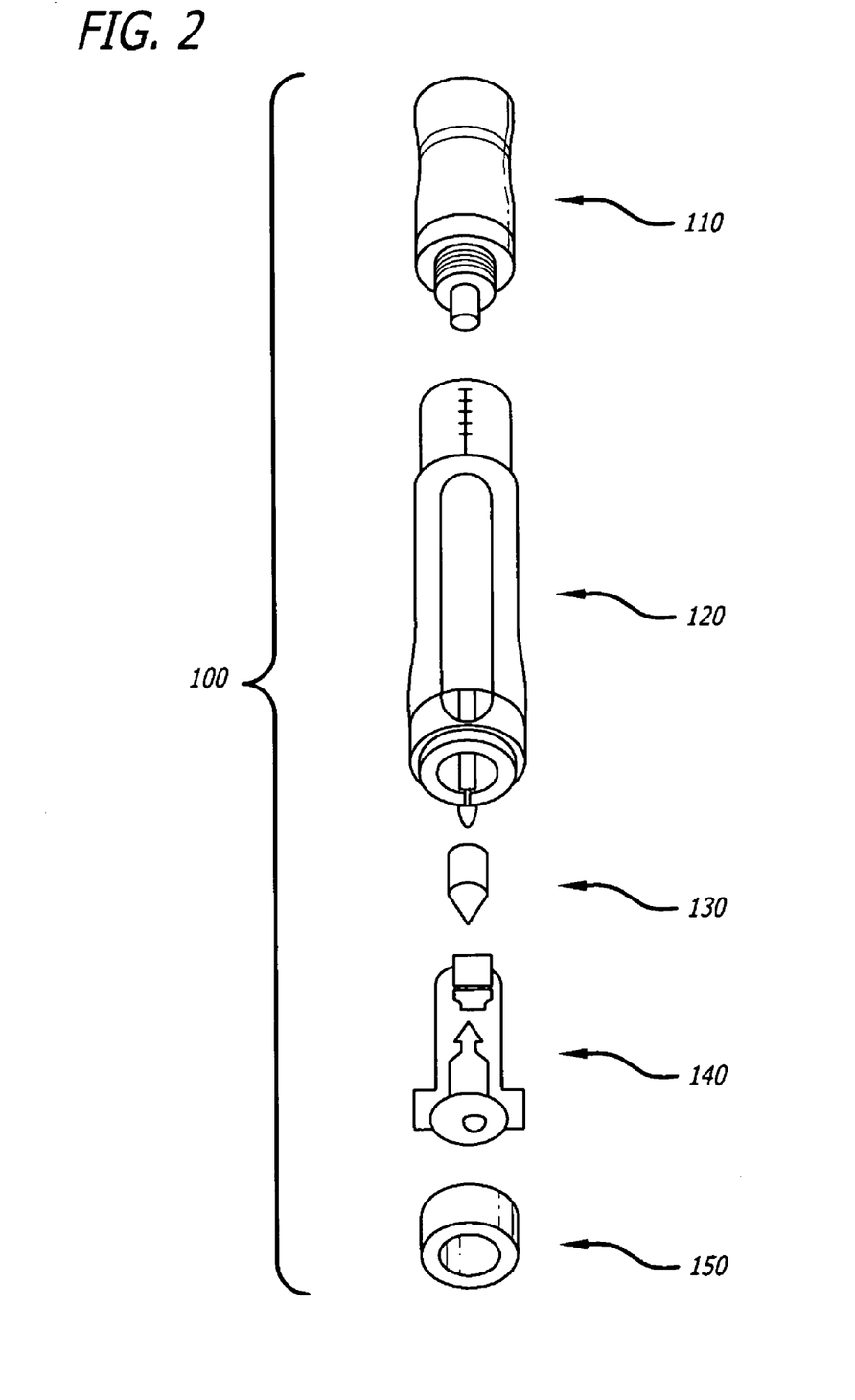
FIG. 2 is a general depiction of a needle-free jet injector that is useful for precision injection of fairly viscous dermal fillers.

Many designs for needle-free injectors are well known in the art. For example, U.S. Pat. Nos. 4,790,824, 5,312,335, 5,911,703, 6,132,395, 7,156,823, 7,029,457 describe a variety of needle-free injector designs and methods of their use, and these descriptions are incorporated herein by reference. FIG. 2 shows one embodiment of a needle-free jet injector 100 of the present invention. The needle-free injector 100 of the present invention may be made of plastic, stainless steel, a combination thereof, or any material or combination of materials that are medically acceptable or known in the art. In one embodiment, the needle-free injector 100 of the present invention is disposable. In another embodiment, the needle-free injector 100 has some disposable parts. The needle-free injector 100 may include a gas pressure source, a power source, a pneumatic compression source, or a combination thereof to drive the ejection of the soft tissue augmentation or dermal filler material from the needle-free injector.

As shown in FIG. 2, the needle-free injector has a chamber or dosage drum 110. The dosage drum 110 can be filled with a volume of soft tissue augmentation material, such as collagen, hyaluronic acid, its salts and mixtures thereof, polysaccharides or any other polymers that are suitable for use as dermal fillers. The collagen and hyaluronic acid used may be of any source known in the art, and may be crosslinked, non-crosslinked, or some combination thereof. In some embodiments, the chamber or dosage drum 110 has an aperture through which soft tissue augmentation or dermal filler material is ejected.

The dosage drum 110 can hold 0.01 ml to 10 ml of soft tissue augmentation material. In one preferred embodiment, the dosage drum 110 holds at least 1 ml of soft tissue augmentation material, such that the dosage drum only has to be filled once to perform a full skin augmentation treatment for one patient. In one preferred embodiment, the dosage drum 110 is a prefilled cartridge containing soft tissue augmentation material.

The needle-free jet injector 100 may further have a main body 120. The main body 120 may be directly connected to the chamber or dosage drum 110, or it may be distantly connected to the dosage drum 100, for example, via rings, bands, or some other body portion. In one embodiment, the dosage drum 110 is housed within the main body 120. The main body 120 may further comprise a compressible spring for ejecting the soft tissue augmentation material. In one embodiment of the present invention, the main body 120 comprises a compressible spring and is further connected to one or more rings. The rings may be of the same or different thicknesses and may be used one at a time or in combination to vary the amount of compression of the spring.

The needle-free injector 100 of the present invention may also have a piston 130. The piston 130 may be used to eject the soft tissue augmentation material from the dosage drum 110. The piston 130 may be operated pneumatically, electronically, and/or through a gas powered source. In one preferred embodiment of the present invention, the piston further works together with a compressible spring or springs for ejecting the soft tissue augmentation material. In another embodiment of the present invention, one or more rings are connected to a compression spring to vary the spring's compression, and a piston is further used to compress the spring in order to eject the soft tissue augmenting material.

In one embodiment of the present invention, the friction of the piston and the compression of the compressing spring are adjusted in order to control the velocity of the ejected soft tissue augmentation material. The ejection velocity of the jet injector should be adjusted such that the soft tissue augmentation material ejects at a rate sufficient to penetrate skin but not to penetrate beyond the cutaneous layers. In one preferred embodiment, the jet injector is adjusted such that it ejects soft tissue augmentation material at a rate of at least 50 m/s. In a further preferred embodiment, the jet injector is adjusted such that it ejects soft tissue augmentation material at a rate of at least 50 m/s but less than 200 m/s.

The needle-free injector 100 may further comprise a nozzle 140 through which a dose of the soft tissue augmentation material is injected. The nozzle diameter affects the diameter of the dose stream and the distance that the dose penetrates into skin. Larger nozzle diameters lead to deeper penetration of soft tissue augmentation materials. In one preferred embodiment, the nozzle diameter of the needle-free injector of the present invention is less than about 500 µm. In a further preferred embodiment, the nozzle diameter of the needle-free injector is less than about 200 µm. In still a further preferred embodiment, the nozzle diameter is less than about 100 µm.

The needle-free injector 100 may also comprise a spacer 150 to separate the nozzle tip from the site of injection. Separation of the nozzle tip from the site of injection on the skin allows for better retention of soft tissue augmentation materials such as hyaluronic acid within the cutaneous layers. Separation of the nozzle tip from the site of injection on the skin also allows for more precise injection of soft tissue augmentation materials. For example, if a deep fold is being filled, a needle-free injector with no spacer or a fairly thin spacer may be used to deposit the soft tissue augmentation material deeper within the skin. If a finer line is being filled, a needle-free injector with a wider spacer may be used so that the majority of the soft tissue augmentation material is deposited less deeply within the skin, and more directly under the line being filled.

The spacer 150 may be made of stainless steel, plastic, or any material compatible with the needle-free injector. The spacer 150 may be a portion on the end of the nozzle 140, integrated with the nozzle itself, or the spacer may be a separate piece that can be selectively attached to the nozzle with screw threads, a quick-connect mechanism, or any other form of attachment. In one embodiment of the present invention, the needle-free injector has a plurality of spacers 150 that are a variety of thicknesses and can be interchangeably attached to the injection end of the needle-free injector 100. In a further embodiment of the present invention, the spacers 150 may be connected to one another as well as to the injection end of the needle-free injector 100. In one preferred embodiment, the needle-free injector comprises a 5 mm spacer. In another preferred embodiment, the needle-free injector comes with at least two interchangeable spacers, ranging in size from 1 mm to 10 mm. In a further preferred embodiment, the needle-free injector comes with at least two interchangeable spacers, ranging in size from 2 mm to 5 mm.

The present invention further relates to kits for soft tissue augmentation. The kits comprise a needle-free injector of the present invention and quantities of soft tissue augmentation material for injection. For example, in one preferred embodiment, a kit of the present invention includes a disposable needle-free injector that comprises a selection of interchangeable spacers ranging from 1 mm to 10 mm in thickness and a nozzle that is less than 200 microns in diameter. The kit further comprises at least 0.01 ml of hyaluronic acid that can be used with the needle-free injector, or more preferably, the kit comprises at least 1 ml of hyaluronic acid. In another preferred embodiment, a kit of the present invention includes a disposable needle-free injector that is prefilled with at least 0.01 ml of hyaluronic acid for injection. In yet another preferred embodiment, the needle-free injector of the present invention comes with disposable cartridge that is prefilled with a quantity of soft tissue augmentation material for injection.

The present invention also related to methods for soft tissue augmentation using a needle-free injector for injection of soft tissue augmentation materials such as collagen, hyaluronic acid, or any other polymers that are suitable for use as dermal fillers. In one preferred embodiment, a needle-free injector is used to inject collagen into the skin of a patient to fill the patient's undesired lines, wrinkles, and folds. The needle-free injector used has a nozzle diameter of less than about 500 µm, and more preferably of less than about 200µ. The injection is done at an injection speed of less than about 200 m/s, preferably between about 50 m/s and about 200 m/s, and more preferably about 100 m/s.

In another preferred embodiment, a needle-free injector is used to inject hyaluronic acid into the skin of a patient to fill the patient's undesired lines, wrinkles, and folds. In one preferred embodiment, during injection, the needle-free injector is separated from the site of injection by at least 2 mm. This separation may be achieved by at least one spacer attached to the end of the nozzle. In one preferred embodiment, at least one spacer is attached to the end of the jet injector nozzle such that the nozzle end of the needle-free injector can be separated from the site of injection by about 2 mm to about 10 mm. In a further preferred embodiment, the needle-free injector is separated from the site of injection by about 5 mm with at least one spacer. In yet another preferred embodiment, a needle-free injector with interchangeable spacers is used, such that when a deep fold is being filled with hyaluronic acid, no spacer or a thin spacer of a maximum of about 5 mm thickness is used, but when a finer line is filled, a new spacer or additional spacers are attached to the needle-free injector to separate the nozzle of the injector from the site of injection by no more than about 10 mm. The needle-free injector used has a nozzle diameter of less than about 500 μm, and more preferably less than about 200 μm. The injection is done at an injection speed of less than about 200 m/s, preferably between about 50 m/s and about 200 m/s, and more preferably about 100 m/s.

The depth of penetration of soft tissue augmentation or dermal filler materials injected via a needle-free injector further depends on the injection volume used in each separate injection. Smaller volumes lead to more superficial penetration. To fill finer lines, smaller volumes of soft tissue augmentation material should thus be used. In cases where substantial delivery volumes are required while maintaining superficial penetration, e.g., to fill a long line, it is desirable to perform a series of injections at lower volumes than a single injection at a large volume. To fill a deep fold, a larger volume of soft tissue augmentation material should be injected with each separate injection.

The following, non-limiting examples provide further detail regarding some of the embodiments of the present invention.

Example 1

The following experiment was run to determine appropriate velocity and diameter, as well as control of velocity and diameter, of jets of viscous dermal filler material ejected from a needle-free injector.

A commercial jet injector (Vitajet 3 by Bioject Inc.) was used to create jets of Hylaform® gel, a hyaluronic acid dermal filler available from Allergan, Inc. of Irvine, Calif., collagen, and hydroxypropylmethylcellulose (HPMC) with various diameters and velocities. The velocity of the jet was controlled by adjusting the amount of spring compression as well as the piston friction of the injector. Two plastic rings, having thicknesses of 3 mm and 1.6 mm, were provided with the jet injector for increasing spring compression. The rings were tested in use individually and together.

The nozzles came in two different orifice diameters: 152 μm and 178 μm. These nozzles were modified to increase the range of nozzle diameters studied. Ruby orifice crystals (from Sapphire Engineering) with diameters of 76 μm and 229 μm were used in place of standard orifice crystals. Above 229 μm the crystal was removed and the thermoplastic end of the injector was drilled to a specified diameter to allow for testing a wide range of nozzle diameters.

Pressure inside the chamber was measured using a calibrated piezoelectric transducer (from Dynasen Inc.). The transducer possessed an outer diameter of 0.065", which allowed for minimal disturbance to the flow. The nozzle was altered in several to incorporate the pressure transducer. For example, a hole was drilled in the nozzle so that the pressure transducer could be inserted. Also, a securing ring was added over the nozzle into which the transducer is threaded to hold it in place under high pressure. A charge integrator (from Dynasen Inc.) comprising a 50Ω resister and a 0.1 mF capacitor was used to facilitate pressure measurements. The charge integrator transforms the charge from the piezoelectric transducer into an output voltage, which was read by an oscilloscope (Tektronix, TDS 224). Each transducer was calibrated by Dynasen Inc. and showed a linear relationship between voltage and pressure. Output of the pressure transducer was collected via LabView with a time resolution of 2-100 μs depending on the length of capture.

FIG. 2 shows a typical pressure profile during ejection of Hylaform® gel. Upon release of the spring, the piston is actuated and impacts the Hylaform® gel reservoir. This elevates the pressure in the reservoir, which in turn creates the jet. The pressure decreases slowly with time and eventually drops to the baseline indicating the end of injection.

The average velocity of the jet was determined from the pressure profile. Specifically, the formation and cessation of the jet is visible in the pressure profile. This information was used to determine the ejection time, $\tau_{ejection}$. Average jet velocity is determined using the following equation $$v_{jet}^{av} = \frac{Q}{A_{nozzle}\tau_{ejection}}$$

where $A_{nozzle}$ is the cross-sectional area of the nozzle and Q is the total volume of liquid ejected. This method can be easily combined with penetration. The jet velocities for injections of this example ranged from 90-140 m/s.

A high-speed video camera (Kodak Ektapro 4500 motion analyzer) was used to assess the integrity of the jet. The jets were backlit with a white light source. The images were captured at a frame rate of 18,000 fps. Individual images were captured using an ATI interface (from ATI Technologies, Inc.) and then analyzed to determine the dimensions of the jet penetration using Adobe Photoshop.

Figure 3:
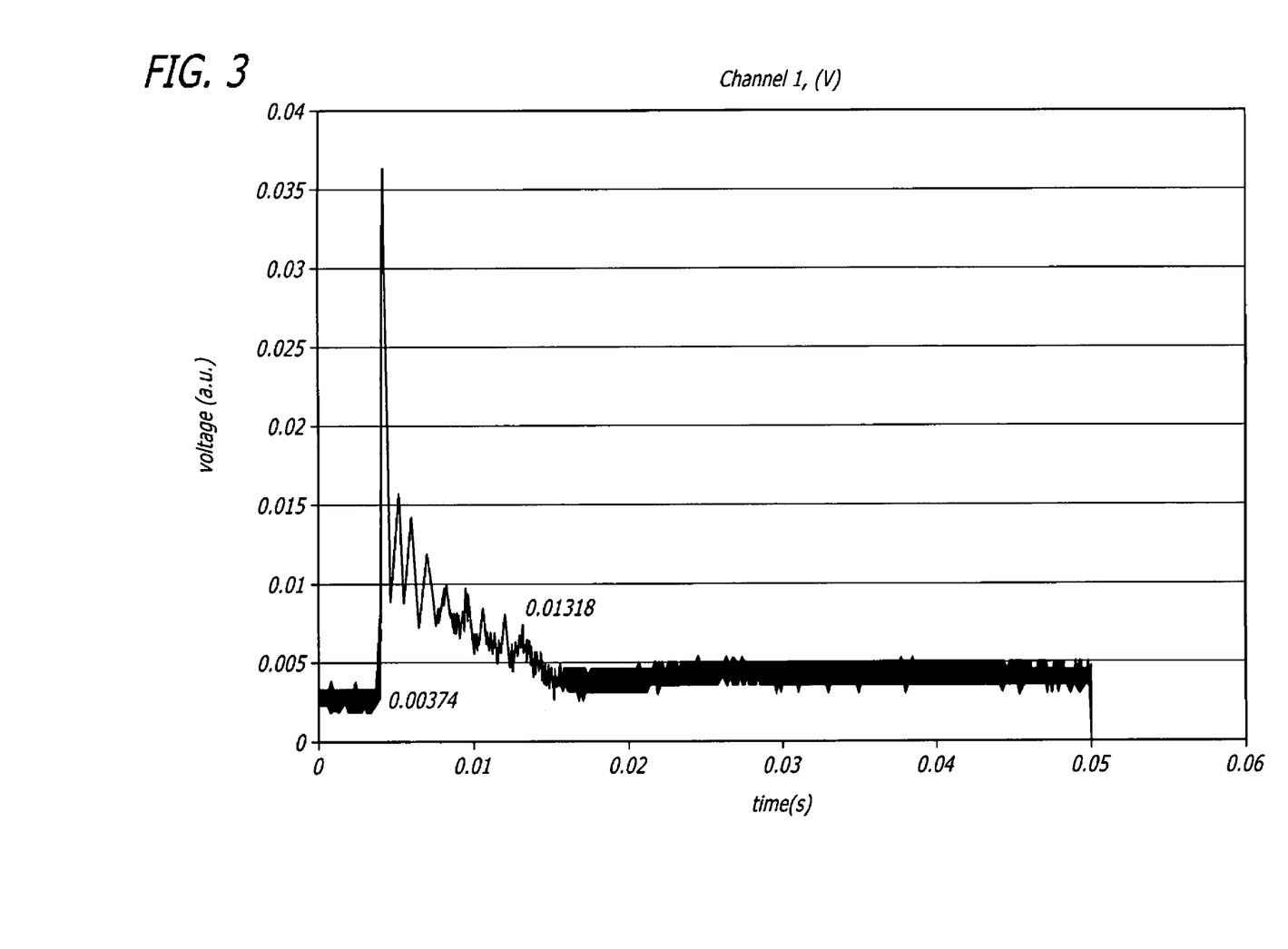
FIG. 3 depicts the pressure profile of a needle-free injector during ejection of Hylaform® gel, a hyaluronic acid dermal filler available from Allergan, Inc. of Irvine, Calif., into air. Numbers below the frames indicate time in milliseconds.
Figure 4:
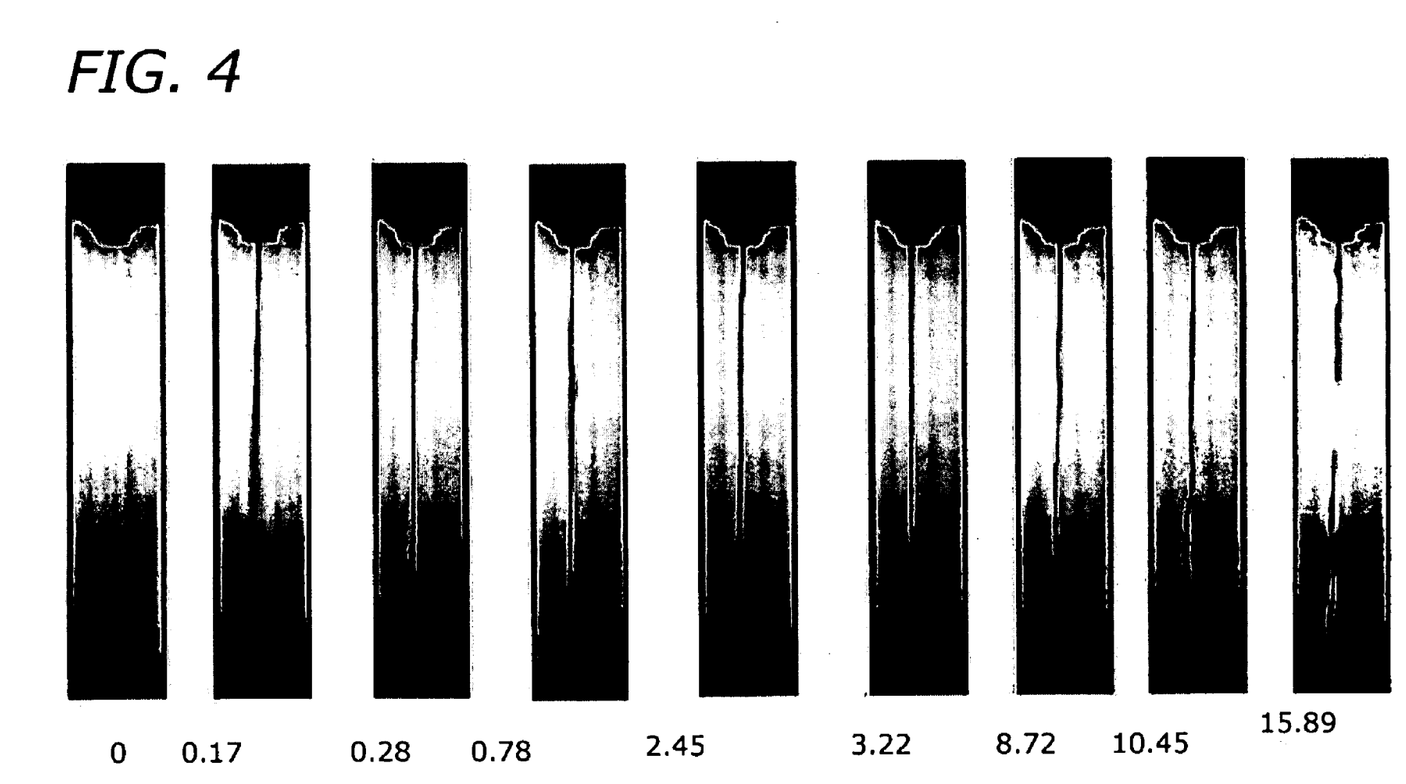
FIG. 4 depicts high speed video of a Hylaform® gel jet. The numbers below the frames show time in milliseconds for progression of the jet.

FIG. 3 shows a series of pictures taken during ejection of Hylaform® gel into air. As can be seen, the Hylaform® gel forms a tight, cylindrical jet that remains fairly rectilinear. Towards the end, the jet shows formation of waves which leads to eventual break-up. FIG. 4 shows frames from a high speed video of Hylaform® gel injection into human skin in vitro. Once again, Hylaform® gel forms a cylindrical jet that makes a clean impact on skin (minimal splash) and deposits material into skin. Formation of a bulge can be clearly seen in later frames.

Example 2

Figure 5:
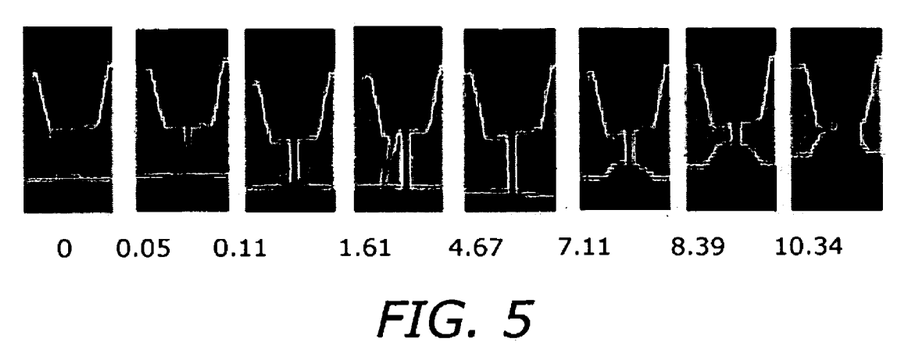
FIG. 5 depicts frames of photographs of the penetration of jet injected Hylaform® gel into human skin. Numbers below the frames indicate time in milliseconds.
Figure 6:
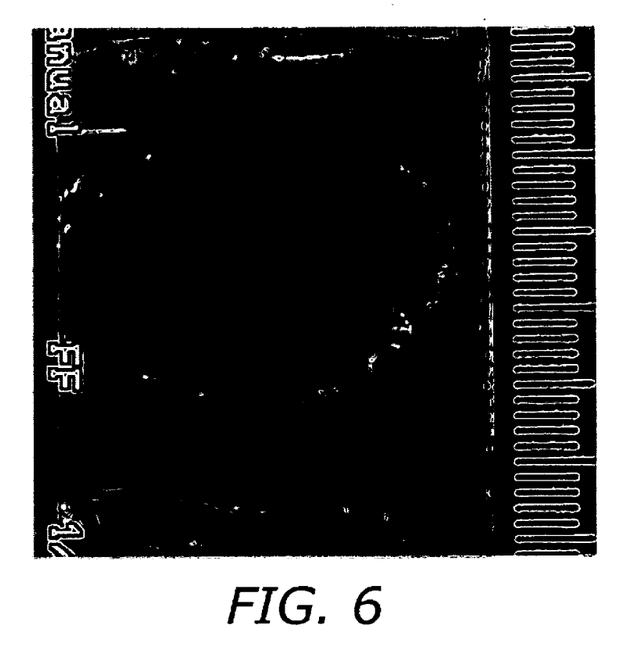
FIG. 6 is a photograph of Hylaform® gel labeled with sulforhodamine B that has been injected with a needle-free jet injector into polyacrylamide gel.

This experiment was run to confirm that fairly viscous dermal fillers could be properly injected into a substantial material. Specifically, the parameters identified in Example 1 were used to inject collagen, HPMC, and Hylafomm® gel into polyacrylamide gels. FIG. 5 shows an example of a Hylaform® gel injection into a polyacrylamide gel. The Hylaform® gel was labeled using sulforhodamine B. The image shows a cylindrical entry region followed by a circular dispersion into the gel.

Example 3

This experiment was run to test various parameters for injecting dermal filler materials into human skin using a needle-free injector.

Human skin was procured through the National Disease Research Interchange. Skin was cleaned to remove fat and subdermal tissues, and was frozen to −70° C. until the time of experiments. All experiments were performed according to institutionally approved protocols. At the time of jet injection, a piece of skin was placed on wax paper and sealed on the sides with medical tape. The skin was supported by a mesh, which was in turn placed on a chamber filled with saline. A 5 mm stainless steel spacing ring was placed on the end of the jet injector nozzle to separate the nozzle from the skin sample.

A model radiolabeled drug, mannitol, was added to the collagen, Hylaform® gel, and HPMC that were injected into the skin samples. To assess mannitol delivery, a solution of $^3$H labeled mannitol (from American Radiolabeled Chemicals, Inc) was added at a concentration of 10 μCi/ml. A volume of about 35 μl was loaded in the injector. A jet was produced at various velocities and diameters using strategies discussed earlier. To detect the amount of mannitol delivered across the skin, skin was placed on a Franz diffusion cell and was injected using a jet injector. A sample of the receiver compartment of the diffusion cell was collected. Once the injection was complete, excess fluid was removed from the top of the skin within one minute and the skin was placed in a scintillation vial. The skin was then dissolved in 2% sodium hydroxide solution (Solvable [Packard]) at 65° C. overnight. The amount of radiation in the skin was determined using liquid scintillation analysis [Tri-carb 2100TR (Packard)]. The scintillation cocktail used for these experiments was Ultima Gold [Packard].

Jet dispersion in skin was visualized by adding SRB to the injected fluid (1.5 mM in DI water). After jet injection, the skin was sectioned near the entry point with a razor blade and imaged using a digital camera. This image was processed using Adobe Photoshop to identify lines of constant luminosity, which were used to determine dimensions of jet dispersion. Due to low diffusion coefficient and low surface adhesion of SRB, the appearance of SRB in the skin is entirely due to jet penetration. Fluid dispersion in the skin is three-dimensional and occurs on a time scale comparable to the time of injection (<1s) as determined by visual observation of the skin prior to sectioning.

The outcome of a jet injection is characterized by several descriptors including penetration depth and completeness (percent of ejected liquid that enters the skin). While the latter plays an important role in determining bioavailability and variability, the former influences issues such as the onset of absorption and possibly pain. Both descriptors are in turn influenced by several jet parameters including exit velocity and nozzle diameter, skin parameters such as mechanical properties and operational parameters such as stand-off distance, e.g. size of the spacer ring.

Figure 7A:
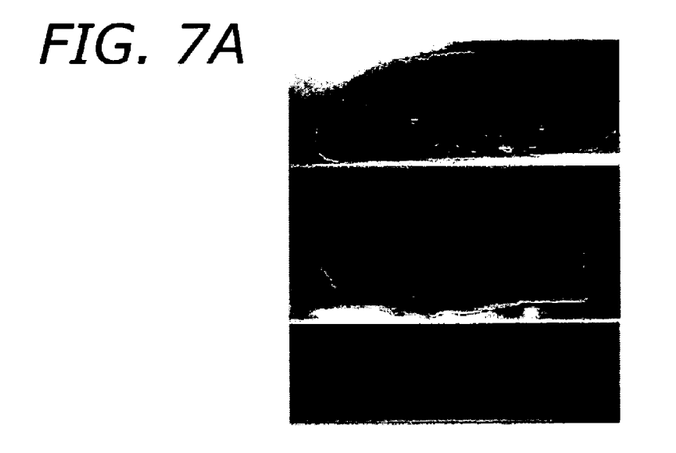
FIG. 7A is a photograph of collagen labeled with sulforhodamine B that has been injected with a needle-free jet injector into human skin in vitro.
Figure 7B:
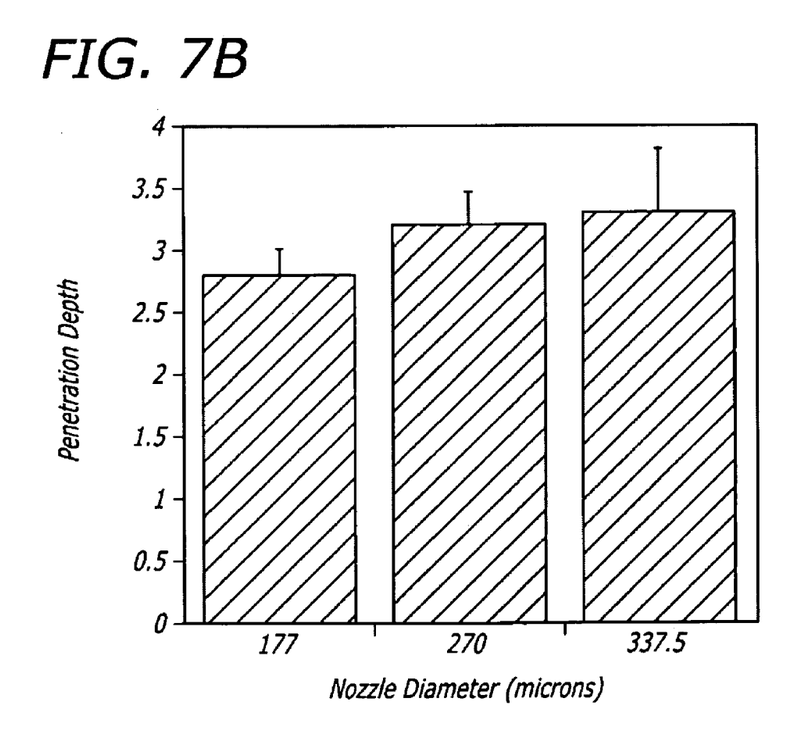
FIG. 7B is a graph depicting the effect of jet injector nozzle diameter on skin penetration of collagen in mm.

As shown in FIGS. 7A and B, the depth of fluid penetration increased with nozzle diameter at a constant velocity. This was consistent across all three materials (Hylaform® gel, collagen, and HPMC) that were injected into skin samples. At a nozzle diameter of 177 μm, jet penetration of collagen was restricted within the superficial skin, while at a nozzle diameter of 337 μm the jet deposited towards the bottom of the dermis. Quantitative data for these images is shown in FIG. 7B.

Without use of the 5 mm spacer, collagen delivered by jet injections using all the tested nozzle diameters was deposited mainly in the skin. A large quantity of the Hylaform® gel, however, penetrated beyond the dermis at most of the nozzle diameters. The 5 mm spacer ring significantly improved deposition of Hylaform® gel within the skin.

Figure 8:
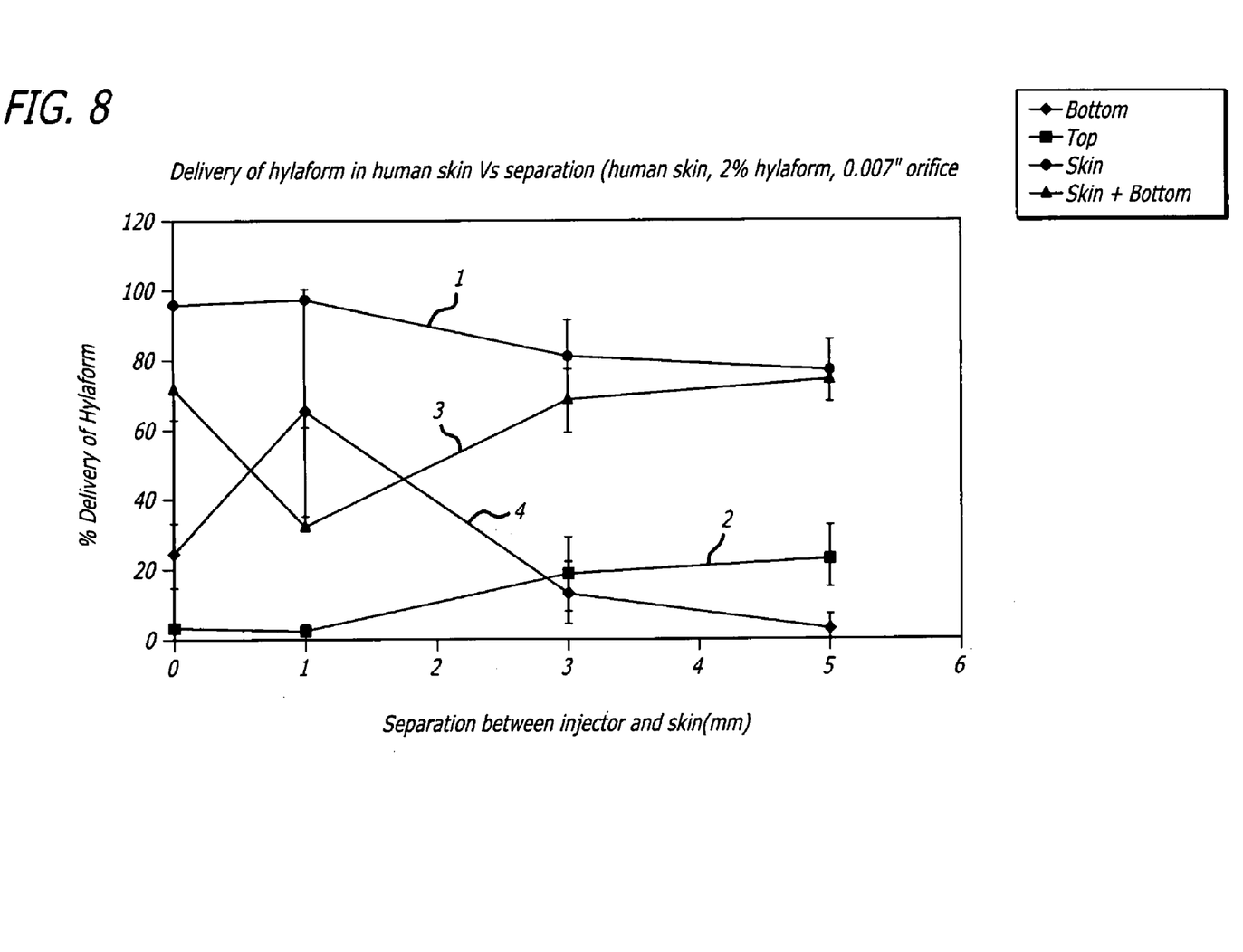
FIG. 8 is a graph depicting depth of needle-free injection of Hylaform® gel labeled with radioactive mannitol into human skin vs. distance of separation of the jet injector tip from the skin that was injected.
Figure 9A:
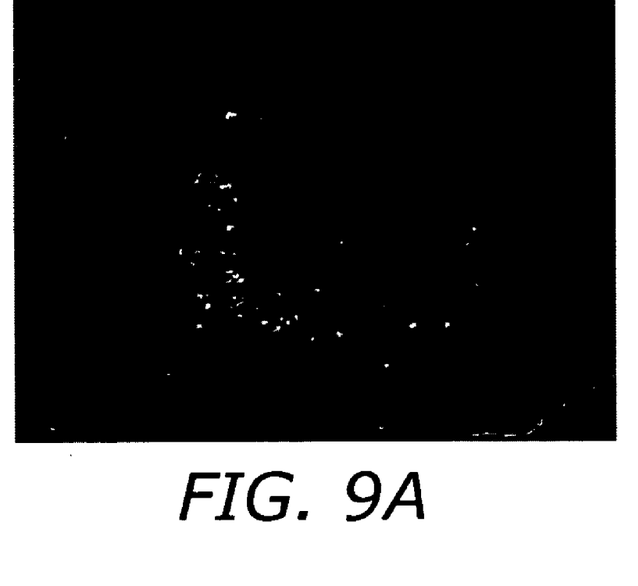
FIG. 9A is a top view of sulforhodamine B labeled Hylaform® gel injected into human skin with a needle-free injector.
Figure 9B:
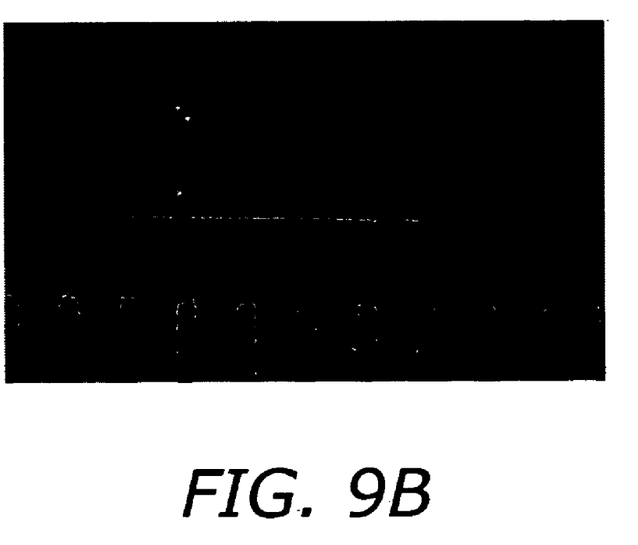
FIG. 9B is a side view of sulforhodamine B labeled Hylaform® gel injected into human skin with a needle-free injector.
Figure 9C:
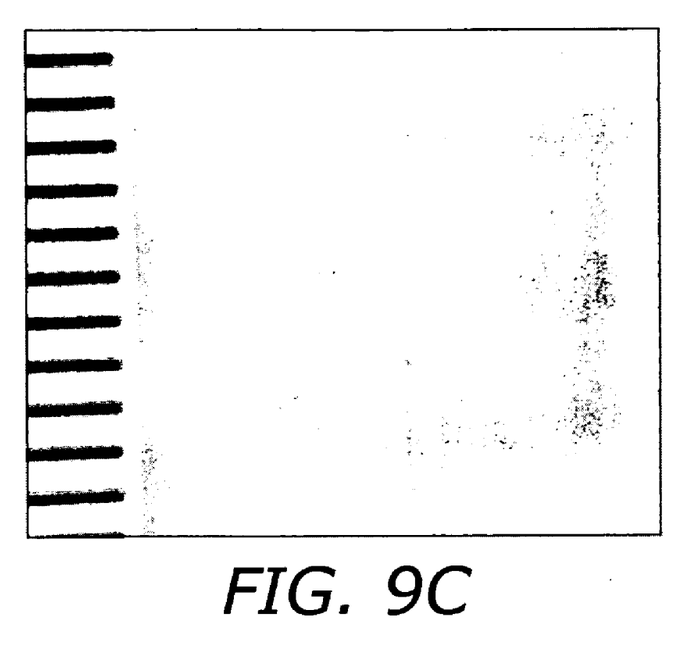
FIG. 9C is a top view of non-labeled Hylaform® gel injection into human skin with a needle-free injector.
Figure 9D:
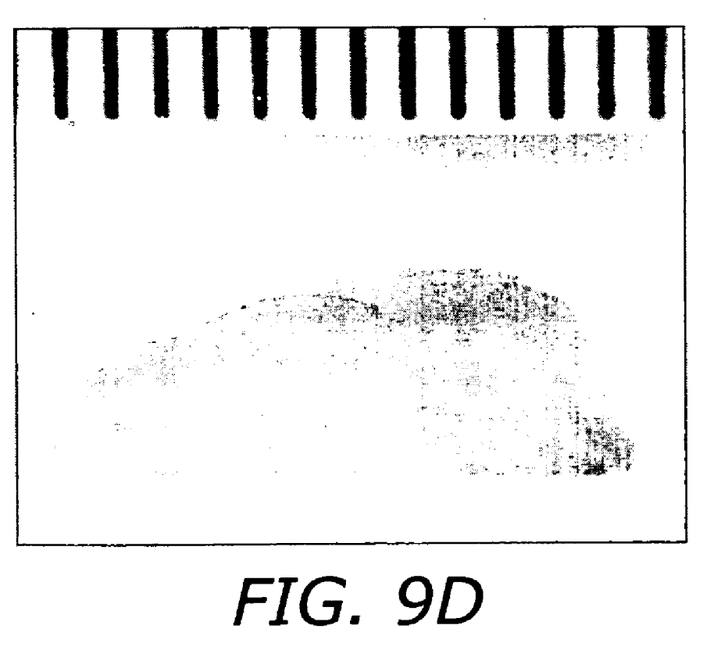
FIG. 9D is a side view of non-labeled Hylaform® gel injection into human skin with a needle-free injector.

FIG. 8 shows injection of radioactive mannitol labeled Hylafomm® gel into the skin, using a jet injector with a 5 mm spacer. The triangle curve 1 shows the total percent of ejected Hylaform® gel that entered the skin. The square curve 2 shows the percent of Hylaform® gel that pooled on the skin's surface. The triangle curve 3 shows the percent of Hylaform® gel that was retained in the skin. The diamond curve 4 shows the percent of Hylaform® gel that penetrated beyond the dermis. The x-axis is the distance between the injector and skin. At a separation of 5 mm, nearly 80% of the ejected dose entered the skin and was retained in it, and less than 5% penetrated beyond the skin's surface. FIGS. 9A, 9B, 9C, and 9C show top and side views of skin injected with Hylaform® gel.

Although only a few embodiments of this invention have been described above with a certain degree of particularity, those skilled in the art could make numerous alterations to the disclosed embodiments without departing from the spirit or scope of this invention. It is intended that all matter contained in the above description or shown in the accompanying drawings shall be interpreted as illustrative only and not limiting. Changes in detail may be made without departing from the spirit of the invention as defined in the appended claims.

What is claimed is:

1. An apparatus for needle-free injection of a soft tissue augmentation material into the skin of a patient, which comprises:
    a main body comprising a chamber for containing the soft tissue augmentation material;
    a drive mechanism for exerting forces on the soft tissue augmentation material in said chamber to expel the soft tissue augmentation material; and
    a nozzle having a first end and a second end, the first end being connected to the main body and said second end located distal to said main body; and
    a plurality of interchangeable spacers of different sizes each being connectable to the second end of the nozzle, including a relatively thin spacer and a relatively wide spacer, wherein the relatively thin spacer, when connected to the second end of the nozzle, facilitates deposit of dermal filler material relatively deeply within the skin and the relatively wide spacer, when connected to the second end of the nozzle, facilitates deposit of dermal filler material relatively less deeply within the skin and wherein each of the spacers is connected to each other spacer.

2. The apparatus of claim 1 further comprising a cartridge prefilled with at least one soft tissue augmentation material, wherein said cartridge can be inserted into said chamber.

3. The apparatus of claim 2 wherein the cartridge is prefilled with a soft tissue augmentation material comprising hyaluronic acid or collagen.

4. The apparatus of claim 1 wherein the relatively thin spacer is at least 1 mm wide.

5. The apparatus of claim 1 that is disposable, and wherein said chamber is filled with a soft tissue augmentation material comprising hyaluronic acid or collagen.

6. The apparatus of claim 1 wherein at least one spacer is connected to the nozzle with screw threads.

7. The apparatus of claim 1 wherein the spacers are connected to one another with screw threads.

8. A needle-free injector for injecting dermal fillers into the skin of a human patient, comprising:
    a main body;
    a dosage drum connected to the main body;
    a nozzle with a first end and a second end having a diameter of less than about 500 μm, wherein the first end is capable of connecting to the main body and the second end is distal to the first end; and
    a plurality of interchangeable spacers of different sizes each being connectable to the second end of the nozzle, including a relatively thin spacer and a relatively wide spacer, wherein the relatively thin spacer, when connected to the second end of the nozzle, facilitates deposit of dermal filler material relatively deeply within the skin and the relatively wide spacer, when connected to the second end of the nozzle, facilitates deposit of dermal filler material relatively less deeply within the skin and wherein each of the spacers is connected to each other spacer.

9. The needle-free injector of claim 8 wherein the relatively thin spacer is at least 1 mm wide.

10. The needle-free injector of claim 9 wherein the relatively thin spacer is at least about 5 mm wide.

11. The needle-free injector of claim 8 where the plurality of spacers range in size from about 1 mm to about 10 mm.

12. The needle-free injector of claim 8, wherein the dosage drum is prefilled with a quantity of a dermal filler material.

13. The needle-free injector of claim 12, wherein the dermal filler material comprises hyaluronic acid or collagen.

14. A method of filling undesired folds, wrinkles, or lines in a patient, comprising using the needle-free injector of claim 8 to administer a dermal filler to an undesired fold, wrinkle, or line of the patient.

15. The method of claim 14 further comprising selecting at least one spacer of the plurality of spacers based on a desired depth of injection of the dermal filler material and connecting the at least one spacer to the second end of the nozzle before filling the undesired fold, wrinkle, or line of a patient.

16. The needle-free injector of claim 8 wherein the at least one spacer is connected to the nozzle with screw threads.

17. The needle-free injector of claim 8 wherein the spacers are connected to one another with screw threads.

18. A kit for soft tissue augmentation, the kit comprising:
a needle-free apparatus comprising a main body with a chamber for containing the soft tissue augmentation material, a drive mechanism for exerting forces on the soft tissue augmentation material in said chamber to expel the soft tissue augmentation material, and a nozzle having a first end and a second end, the first end being connected to the main body and said second end located distal to said main body;
a quantity of at least one soft tissue augmentation material and
a plurality of interchangeable spacers of different sizes each being connectable to the second end of the nozzle, including a relatively thin spacer and a relatively wide spacer, wherein the relatively thin spacer, when connected to the second end of the nozzle, facilitates deposit of dermal filler material relatively deeply within the skin and the relatively wide spacer, when connected to the second end of the nozzle, facilitates deposit of dermal filler material relatively less deeply within the skin and wherein each of the spacers is connected to each other spacer.

19. The kit of claim 18, wherein the at least one soft tissue augmentation material comprises hyaluronic acid or collagen.

20. The kit of claim 19, wherein the nozzle of the needle-free apparatus has a diameter of less than 200 μm.

21. The kit of claim 19, wherein the hyaluronic acid or collagen is contained within at least one cartridge that can be inserted into the chamber of the needle-free apparatus.

22. The kit of claim 18, wherein the needle-free apparatus is disposable.

23. The kit of claim 22, wherein the needle-free apparatus is prefilled with a quantity of the at least one soft tissue augmentation material.

24. A method for augmenting soft tissue of a patient, comprising filling the needle-free apparatus of the kit of claim 18 with the at least one soft tissue augmentation material and injecting the at least one soft tissue augmentation material with the needle-free injector to augment the soft tissue of a patient.

25. A method for augmenting soft tissue of a patient, comprising selecting at least one spacer of the plurality of spacers of the kit of claim 18 based on a desired depth of injection of the augmentation material, connecting the selected spacer to the second end of the nozzle, placing the connected spacer against a portion of skin of a patient, and using the needle-free injector to inject a volume of the hyaluronic acid into the portion of skin.

26. The kit of claim 18 wherein the wherein at least one spacer is connected to the nozzle with screw threads.

27. The kit of claim 18 wherein the spacers are connected to one another with screw threads.

28. A kit for soft tissue augmentation, the kit comprising:
a needle-free apparatus comprising a main body with a chamber for containing the soft tissue augmentation material, a drive mechanism for exerting forces on the soft tissue augmentation material in said chamber to expel the soft tissue augmentation material, and a nozzle having a first end and a second end, the first end being connected to the main body and said second end located distal to said main body;
a quantity of at least one soft tissue augmentation material and
a plurality of interchangeable spacers of different sizes each being connectable to the second end of the nozzle, including a relatively thin spacer and a relatively wide spacer, wherein the relatively thin spacer, when connected to the second end of the nozzle, facilitates deposit of dermal filler material relatively deeply within the skin and the relatively wide spacer, when connected to the second end of the nozzle, facilitates deposit of dermal filler material relatively less deeply within the skin;
wherein at least one of the spacers is connected to the second end of the nozzle with screw threads and wherein each of the spacers is connected to each other spacer with screw threads.

* * * * *